United States Patent [19]

Deboeck

[11] Patent Number: 4,847,282

[45] Date of Patent: Jul. 11, 1989

[54] MUCOLYTIC ACETYLCYSTEINE SALTS

[75] Inventor: Arthur M. Deboeck, Herne, Belgium

[73] Assignee: Galephar, Molenbeek, Belgium

[21] Appl. No.: 106,005

[22] Filed: Oct. 7, 1987

Related U.S. Application Data

[63] Continuation of Ser. No. 867,403, May 13, 1986, abandoned, which is a continuation of Ser. No. 728,773, Apr. 30, 1985, abandoned, which is a continuation of Ser. No. 485,434, Apr. 15, 1983, abandoned.

[30] Foreign Application Priority Data

Apr. 19, 1982 [LU]  Luxembourg .......................... 84095

[51] Int. Cl.$^4$ ................ A61K 31/205; A61K 31/405; C07D 233/64
[52] U.S. Cl. .................... 514/400; 514/554; 548/344; 562/557
[58] Field of Search ....................... 548/344; 562/557; 260/501.12; 514/400, 554

[56] References Cited

U.S. PATENT DOCUMENTS 3,184,505  5/1965  Martin et al. ........................ 562/557

OTHER PUBLICATIONS

Chemical Abstracts, 43:4710a (1949).
Chemical Abstracts, 82:103136w (1975).
Chemical Abstracts, 91:1250925 (1979).
Chemical Abstracts, 94:36376g (1981).
Rohdewald, et al., Thermochimica Acta, 49, 101 (1981).
The Medical Letter, vol. 12, No. 6, 3/20/70.
P. Duchatelet, et al, Acta Therapeutica, 13, 579–586 (1987).
S. Rao, et al., Am. Rev. Resp. Dis., 102, 17–22 (1970).
G. Dano, Acta Allergologica, 1971, 26, 181–190.
S. Ho, et al, Br. Med. J., 287, 876–877 (1983).
J-C Cazin, Studies of Acute Toxicity on Mouse and Rat of N-Acetylcysteine and Lysine N-Acetylcysteinate, etc., Lille, France, 2/4/85.
Kovach, I., et al., J. Pharm. Sci., 64(6), 1070–1071 (1975).

Primary Examiner—Richard A. Schwartz
Attorney, Agent, or Firm—Kenyon & Kenyon

[57] ABSTRACT

Water-soluble acetylcysteine salts, useful as mucolytic agents, consisting of reaction products of acetylcysteine with at least one basic amino-acid, the latter being preferably selected from the group comprising arginine, lysine, histidine, ornithine and glycine.

5 Claims, No Drawings

MUCOLYTIC ACETYLCYSTEINE SALTS

This application is a continuation of U.S. patent application Ser. No. 867,403, filed May 13, 1986, now abandoned, which is a continuation of U.S. patent application Ser. No. 728,773, filed Apr. 30, 1985, now abandoned, which is a continuation of U.S. patent application Ser. No. 485,434, filed Apr. 15, 1983, now abandoned.

This invention relates to pharmaceutically acceptable water-soluble acetylcysteine salts.

Acetylcysteine or N-acetyl-L-cysteine is a well known drug, more particularly useful for its mucolytic properties and as antidote against acute intoxication with paracetamol. However, it has the drawback to be only very slightly soluble in water, which impedes its use in most pharmaceutical forms. For that purpose, alkali metal salts may be prepared but they have the drawback to bring with themselves, alkaline ions including sodium, which often are unsuitable.

This invention has for its object to provide a highly water-soluble acetylcysteine salt which does not have the drawbacks of the alkali metal salts.

It is also an object of this invention to provide a water-soluble acetylcysteine salts which are characterized by useful mucolytic properties and which do not produce undesirable side-effects when administered therapeutically.

To this end, according to the invention, the salt consists of the reaction product of acetylcysteine with at least one basic amino-acid.

The salts of this invention possess important advantages over other such mucolytic agents. When administered therapeutically, the salts of this invention are notably less likely than other similar mucolytic agents to produce bronchiospasms. This is a substantial and unexpected advantage over the prior art.

Advantageously, this salt contains about 1 to 5 moles, and preferably about 1 mole of basic amino-acid per mole of acetylcysteine.

The basic amino-acid or amino-acids used may be natural or not, such as, for example arginine, lysine, histidine, ornithine or glycine. The basic amino-acids according to the invention can include one or more asymmetrical centers and in this connection they can exist as optically active isomer forms. It should be cleary understood that the invention includes both epimer forms, such as the levorotary and dextrorotary forms, as well as mixture thereof. Examples of levorotary and extrorotary basic amino-acids are D- and L-lysines and D- and L-arginines.

The invention also concerns the preparation of said acetylcysteine salts.

According to a first way of proceeding, acetylcysteine is reacted with an aqueous solution containing the basic amino-acid or amino-acids. After reaction, water is then separated from the reaction mixture so obtained by suitable separation methods, such as by evaporation or lyophilization.

Another way of proceeding consists of reacting an aqueous or hydro-organic solution or dispersion containing the amino-acids or amino-acids with an organic solution or dispersion containing acetylcysteine with an aqueous solution containing acetylcysteine or with acetylcysteine as such, and separating the solvent from the reaction mixture so obtained by suitable separation methods, such as by filtration, lyophilization or evaporation. Examples of organic solvents used for dissolving the amino- acids and acetylcysteine are polar organic solvents, such as alcohols, glycols, polyglycols, ketones, dimethylformamide and dimethylsulfoxide. Mixtures of such solvents can also be used.

A third way of proceeding consists of bringing into contact a salt or salts of the basic amino-acid or amino-acids in aqueous organic or hydroorganic solution with acetylcysteine in aqueous, organic or hydro-organic solution, and separating the solvent from the reaction mixture by suitable separation methods,such as by evaporation, lyophilization or filtration. An example of amino-acid salt is lysine carbonate. Examples of precipitation solvents are alkyl acetates, sulfuric ether, dioxane, tetrahydrofuran, ketones, alcohols, and mixtures thereof.

Another way of proceeding consists of thoroughly mixing to dryness the solid reactants,i.e. the basic amino-acid or amino-acids or salts thereof with acetylcysteine . The so obtained powder is immediately usable for making preparations to be dissolved at the time of use. In case of the carbonate of an amino-acid or an amino-acid mixture is used, the powder obtained, after admixture of a pharmaceutically acceptable acid or a mixture of pharmaceutically acceptable acids, allows to obtain effervescent preparations.

According to the invention, in all these four ways of proceeding, said treatment is carried out at a temperature of about $-5°$ C. to 100° C., and preferably at a temperature of about 20° C.

Acetylcysteine is a slightly water-soluble solid thioacid. As already above-mentioned, salts are easily obtained with basic amino-acids, such as arginine, lysine, histidine and ornithine.

The quite water-soluble salts of acetylcysteine require between 0.5 and 5 molecules, preferably 1 molecule of amino-acid per acetylcysteine molecule.

As a matter of fact, the acetylcysteine salts of the invention have the following formula :

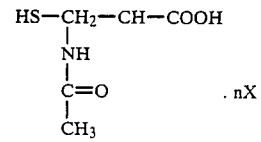

wherein n, being the number of amino-acid molecules per molecule of acetylcysteine, is comprised between 1 and 5, preferably between 1 and 2, and X is the amino-acid or the amino-acids.

The hydrosoluble acetylcysteine salts of the present invention may thus be obtained by using known salt preparation methods, and particularly, by bringing into aqueous, hydro-organic or organic solution or suspension one or several amino-acids, or by bringing into aqueous, hydro-organic or organic solution or suspension one or several amino-acid salts to which, while keeping the temperature between 0° C. and 100° C., preferably at about 20° C., is added under stirring by small portions the required amount of acetylcysteine, optionally as organic, hydro-organic or aqueous solution. To this end, it should be noted that the addition sequence of the concerned reactants may be reversed.

When the solution becomes clear, the solvent is removed from the reaction mixture by any suitable separation methods, such as, for example, by lyophilization (aqueous solution) or by moderate heating under vacuum. A water-soluble powder is so obtained, which may be used for preparing solid forms (tablets, suppositories, lozenges, granules, sugar-coated pills) and injectable forms. It is obvious that the solutions of acetylcysteine salts, prepared as hereinafter explained, may be used immediately as injectable form without being previously lyophilized, provided that their ionic strength is acceptable or rendered so.

Hereinafter some non-limitative examples for preparing compounds according to the invention are given.

EXAMPLE 1

To an aqueous solution containing 6.75 g of lysine base in 100 ml of water, 7.58 g of acetylcysteine are added gradually and under stirring . The pH is adjusted at 6.5 by adding either acetylcysteine or lysine base. The so obtained solution is frozen and lyophilized. 14.3 g of lysine acetylcysteinate instaneously water-soluble and having the following characteristics are obtained:

Melting point: 290°–295° C. (decomposition)
Solubility: higher than 30%.

By proceeding in the same way with arginine, histidine or ornithine, the corresponding salts all of them being water-soluble are obtained.

EXAMPLE 2

To a solution of 14.6 g of lysine base in 10 ml of water and 50 ml of methanol, 16.3 g of acetylcysteine are added by small portions. After a reaction period of about 1 hour, the solution is evaporated to dryness. The so obtained white powder is triturated with 100 ml of ethanol and filtered off. After drying lozenges (pellets), tablets, capsules, compressed tablets, solutions, syrups, emulsions containing traditional additives or excipients in galenic industry are used. These galenical forms may release the active agent in a normal or a time-programmed way.

The salts of the present invention may also be administered as aerosals or sprays, acetylcysteinate being either dissolved in a suitable solvent or as a powder.

For parenteral administration, any suitable vehicle will be used, such as, for example, sterile water, peanut oil or ethyl oleate.

For rectal administration, suppositories, rectal capsules, solutions or gels will be used.

The active compound may be administered alone or in combination with other active products having a similar or different activity.

The recommended doses are, for example, 100 mg to 20 g, advantageously 500 ml to 10 g per day orally and rectaly.

I claim:

1. A water-soluble acetylcysteine salt, useful as a mucolytic agent, which is the reaction product of acetylcysteine and one or more amino acids selected from the group comprising arginine, lysine, histidine, ornithine and glycine.

2. A salt as a claim 1, which contains about 1 to 5 moles of basic amino-acid per mole of acetylcysteine.

3. A salt as in claim 2, which contains about 1 mole of basic amino-acid per mole of acetylcysteine.

4. A pharmaceutical composition for use as a mucolytic agent comprising as active product a therapeutic amount of at least one water-soluble aceytlcysteine salt according to any of claims 1 to 3, in association with at least a suitable excipient.

5. A method of use of acetylcysteine salt according to any of claims 1 to 3 or of the composition according to claim 4, as mucolytic agent or antidote against acute intoxication with paracetamol, which comprises administration of acetylcysteine salts orally, parenterally or rectaly to a host at daily doses of 100 mg to 10 g.

* * * * *